US006436227B1

(12) United States Patent
Adler

(10) Patent No.: US 6,436,227 B1
(45) Date of Patent: Aug. 20, 2002

(54) METHOD AND COMPOSITION FOR REMOVING ADHESIVE BANDAGES

(76) Inventor: Mauricio Adler, 203 Avenue F, Brooklyn, NY (US) 11218

( * ) Notice: Subject to any disclaimer, the term of this patent is extended or adjusted under 35 U.S.C. 154(b) by 0 days.

(21) Appl. No.: 09/531,460

(22) Filed: Mar. 20, 2000

Related U.S. Application Data

(63) Continuation-in-part of application No. 09/024,737, filed on Feb. 17, 1998, now Pat. No. 6,063,231.
(60) Provisional application No. 60/055,289, filed on Aug. 13, 1997.

(51) Int. Cl.⁷ .......................... A61M 35/00; B32B 35/00
(52) U.S. Cl. ..................... 156/344; 604/289; 604/290; 510/134
(58) Field of Search ................................ 156/344, 584; 604/289, 290, 307; 602/54, 57; 510/134

(56) References Cited

U.S. PATENT DOCUMENTS

| 2,539,531 | A | * | 1/1951 | Clensos ..................... 510/134 |
| 2,552,520 | A | * | 5/1951 | Coler ......................... 510/134 |
| 5,004,502 | A | * | 4/1991 | Ramzan .................. 106/287.13 |
| 5,146,938 | A | * | 9/1992 | Lutener et al. ............... 134/32 |
| 5,188,754 | A | * | 2/1993 | Weltman et al. ........... 510/106 |
| 5,308,531 | A | * | 5/1994 | Urfer et al. ............. 252/174.17 |
| 5,609,678 | A | * | 3/1997 | Bergman .................... 106/311 |
| 5,783,551 | A | * | 7/1998 | Mirsky ....................... 510/407 |
| 5,965,518 | A | * | 10/1999 | Nakatsu et al. ............. 424/401 |
| 6,063,231 | A | * | 5/2000 | Adler et al. ................. 156/344 |

* cited by examiner

*Primary Examiner*—Mark A. Osele
(74) *Attorney, Agent, or Firm*—William L. Krayer

(57) ABSTRACT

Methods and compositions for loosening adhesive bandages on human skin include d-limonene and, preferably, alkyl benzoates.

5 Claims, No Drawings

METHOD AND COMPOSITION FOR REMOVING ADHESIVE BANDAGES

RELATED APPLICATION

This application is a continuation-in-part of application Ser. No. 09/024,737, now U.S. Pat. No. 6,063,231 filed Feb. 17,1998, which claims the benefit of Provisional Application Ser. No. 60/055,289 filed Aug. 13, 1997, both in the names of Mauricio Adler and Daniel Kruh.

TECHNICAL FIELD

This invention relates to a method and composition for removing adhesive bandages from people to minimize pain during the process of removal.

BACKGROUND OF THE INVENTION

Adhesive bandages are well known for their tenacity and excellent adhesion to the skin. They are widely used in the form of small packaged combinations of adhesive tape and sterile gauze, and are commonly applied by medical personnel in the form of sterile pads or gauze over the wound or sore, held in place by the adhesive tape which is wound or cut to cover both the sterile gauze and the nearby skin.

An unpleasant side effect of the excellent service of adhesive tape is the painful step of removing it. Breaking the bonds of adhesion to the skin is not the only source of pain; if there is hair on the skin under the adhesive tape, which is quite common, the hair also adheres to the tape and is pulled—sometimes pulled out by the root—when the tape is removed.

In spite of the widespread use of adhesive bandages and adhesive tape for medical purposes, very little attention has been paid to the problem of alleviating the infliction of pain when the bandages and tape are removed. This is so also in spite of the fact that adhesive solvents and removers are known in other contexts.

For example, in U.S. Pat. No. 5,604,193, an adhesive and enamel remover is described containing d-limonene, certain dibasic esters, and N-methyl pyrrolidone. The composition is suggested for removing adhesive residues and enamels from various building surfaces and the like.

D-limonene is combined with tetrahydrofurfuryl alcohol in U.S. Pat. No. 5,514,294, an all-purpose cleaner containing d-limonene is >described in U.S. Pat. No. 4,620,937, and a skin cleaner containing d-limonene is described in U.S. Pat. No. 5,063,062. A small amount of lanolin is included with a limonene in a hydrocarbon base in U.S. Pat. No. 3,933,674 (Re 29,649.)

While d-limonene has been known for use in general cleaning compositions and has been shown to be relatively safe for humans (see, for example, the above-mentioned U.S. Pat. No. 3,933,674 which suggests use of its particular composition for removing the residues of dental impression materials—col 2, line 22), the art has not seen the advantages of using d-limonene in a composition for removing adhesive tape from human skin.

SUMMARY OF THE INVENTION

My invention is the use of d-limonene, alone or together with an appropriate solvent or carrier, or more than one solvent or carrier, to aid in the removal of adhesive tape from human skin. The tape may be in the form of prepackaged bandages or patches, or simply from a roll as applied by a physician, nurse or other medical attendant or even a lay person.

D-limonene has the Chemical Abstracts Number 5989-27-5. It is also known as p-mentha-1, 8-diene, 4-isopropenyl-1-methylcyclohexene, and 1-methyl-4-(1-methyleneyl)cyclohexene, and more commonly orange oil, cinene, menthadiene, or citrus oil. It occurs in the skins of citrus fruits, particularly oranges. Its structural formula is

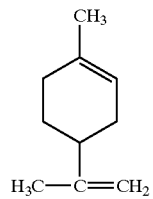

Although "orange oil" may not be pure d-limonene, it is considered totally interchangeable with and the same as d-limonene herein.

My preferred composition contains at least about 20% by weight of d-limonene, with the balance being non-toxic solvents and/or carriers, and/or oils or other materials known to be soothing to the skin.

The composition is applied to the portion of the adhesive tape which is adhering to the skin, and permitted to soak into it for a short period of time, typically about a minute. The d-limonene will soften and swell the adhesive on the tape and at the interface with the skin, neutralizing its tackiness and adherent characteristics. The tape can then be easily removed by gently or abruptly pulling on it.

DETAILED DESCRIPTION OF THE INVENTION

My method is a method of removing adhesive tape adhering to human skin comprising applying to said adhesive tape a composition comprising d-limonene, permitting said composition to soak into said tape, and pulling on said tape to remove it from said human skin. More particularly, the method comprises applying to the adhesive tape a composition comprising at least about 20% d-limonene by weight, permitting said composition to soak into said tape, and pulling on said tape to remove it from said human skin. The composition is preferably permitted to soak into the tape for at least about thirty seconds, most preferably at least two minutes.

A variety of solvents and carriers can be used with the d-limonene, but isopropanol is preferred for its widespread approval and its well-known antimicrobial properties.

Preferably, the composition will comprise 20–80% by weight d-limonene, about 10–60% by weight isopropyl alcohol, and about 10–60% by weight $C_{7-20}$ hydrogenated naphthenes and isoparaffins. Within the class of $C_{7-20}$ hydrogenated naphthenes and isoparaffins, I prefer to use the commercially available "Isopar L", which has the Chemical Abstracts Number CAS 64742-48-9; it is a clear, water-white, almost odorless liquid, available from Exxon Chemical Company, Houston, Texas. Isopar H; comprising $C_{7-20}$ isoparaffins, and Isopar K are similar, miscible with d-limonene, and also can be used in my invention.

Most preferably, the composition comprises 32–38% d-limonene, 32–38% $C_{10-13}$ hydrogenated naphthenes and isoparaffins, and-the balance isopropanol, the percentages being by weight. Other useful variants of the composition include (a) a 1:1:1 by weight mixture of d-limonene, Isopar L, and isopropyl alcohol, (b) a mixture by weight of 37.5% d-limonene, 37.5% Isopar L, and 25% isopropanol, and (c)

a 1:1 by weight mixture of d-limonene and Isopar L; this may vary in the range of 20:80 to 80:20 parts by weight d-limonene and $C_{10-13}$ hydrogenated naphthenes and isoparaffins.

Combinations of the Isopars mentioned above and d-limonene, with and without isopropanol, have successfully swollen and detackified a variety of medical adhesives and adhesive tapes containing materials such as polyisobutylene, ethylene-vinyl acetate copolymers, polydimethylsiloxane, polyisoprene, styrene-isoprene styrene block copolymers, styrene-butadiene-styrene block copolymers, and acrylate copolymers.

For this continuation-in-part application, a preferred formulation may replace (or be mixed with) the hydrogenated naphthenes and isoparaffins with C12–15 alkyl benzoates. Thus a preferred composition is as follows: (1) alkyl (12–15 carbon atoms) benzoates, 40–50 (preferably 45) parts by weight, (2) d-Limonene, 30–40 parts by weight, (3) and isopropyl alcohol, 10–25 parts by weight, optionally with (4) up to 25 parts by weight other alcohols. An example of ingredient number 4 is SD alcohol 40B, a mixture of alcohols useful in medical applications. Any other alcohols known to be useful in topical human treatment may be used in ingredient 4. More specifically, my preferred composition employs amounts of the ingredients near the middle of the ranges specified. A further composition of this continuation-in-part comprises 20–80 parts by weight d-limonene and 80–20 parts by weight isopropanol. Other solvents, alcohols, and additives as disclosed herein and as are common in lotions and the like may be included with this basic composition in amounts which do not impair the effectiveness of the composition for the purposes recited herein. Generally, the combination of d-limonene and isopropanol will not be less than 25%, preferably not less than 50%, and most preferably not less than 60%, in such compositions. For example, such a composition could contain about 5% to 50% alkyl benzoates wherein the alkyl groups have 12–15 carbon atoms.

The composition(s) of this continuation-in-part may be used in any method or composition described in the parent application and herein. Small amounts of fragrance or other conventional additives for consumer and over-the-counter medical products may also be used. As an example, a fragrance may be used in an amount up to 2.5% or more.

What is claimed is:

1. Composition for conditioning adhesive tape for removal from human skin comprising about 20–80% by weight d-limonene, about 10–60% by weight isopropyl alcohol, and the balance either C12–C15 alkyl benzoates or C7–20 hydrogenated naphthenes or isoparaffins or a mixture thereof.

2. Composition of claim 1 including up to 25 percent alcohols other than isopropyl alcohol.

3. Composition of claim 2 including a small amount of a fragrance.

4. A method of removing adhesive tape adhering to human skin comprising applying to said adhesive tape a composition comprising d-limonene, permitting said composition to soak into said tape, and pulling on said tape to remove it from said human skin, wherein said composition comprises 30–40 percent d-limonene, 40–50 percent alkyl benzoates wherein the alkyl groups have from 12 to 15 carbon atoms, 10–25 percent isopropyl alcohol, and up to 20 percent other alcohols useful in medical applications.

5. A method of removing adhesive tape adhering to human skin comprising applying to said adhesive tape a composition comprising 20–80 parts by weight d-limonene, 80–20 parts by weight isopropanol, and about 5% to about 50% alkyl benzoates wherein the alkyl groups containing 12–15 carbon atoms, permitting said composition to soak into said tape, and pulling on said tape to remove it from said human skin.

* * * * *